United States Patent [19]
Claremon et al.

[11] Patent Number: 5,658,901
[45] Date of Patent: Aug. 19, 1997

[54] 2,3-DIHYDRO-1-(2,2,2,-TRIFLUOROETHYL)-2-OXO-5-PHENYL-1H-1,4-BENZODIAZEPINES

[75] Inventors: David A. Claremon, Maple Glen; Nigel Liverton, Harleysville; Harold G. Selnick, Ambler, all of Pa.

[73] Assignee: Merck & Co., Inc., Rahway, N.J.

[21] Appl. No.: 516,226

[22] Filed: Aug. 17, 1995

Related U.S. Application Data

[63] Continuation-in-part of Ser. No. 292,447, Aug. 18, 1994, abandoned.

[51] Int. Cl.$^6$ .......................... C07D 243/20; A61K 31/55
[52] U.S. Cl. .......................... 514/221; 540/509
[58] Field of Search ................... 514/221; 540/509

[56] References Cited

U.S. PATENT DOCUMENTS

| | | | |
|---|---|---|---|
| 4,470,988 | 9/1984 | Watthey | 424/244 |
| 4,473,575 | 9/1984 | Watthey | 424/263 |
| 4,503,060 | 3/1985 | Walther et al. | 514/214 |
| 4,507,313 | 3/1985 | Braestrap et al. | 548/336 |
| 4,537,885 | 8/1985 | Watthey | 514/183 |
| 4,600,534 | 7/1986 | Bach et al. | 260/239.3 B |
| 4,692,522 | 9/1987 | Parsons et al. | 540/523 |
| 4,775,671 | 10/1988 | Hunkeler et al. | 514/220 |
| 4,820,834 | 4/1989 | Evans et al. | 540/509 |
| 4,847,248 | 7/1989 | Freidinger et al. | 514/214 |
| 4,992,437 | 2/1991 | Naka et al. | 514/220 |
| 5,004,741 | 4/1991 | Evans et al. | 514/221 |
| 5,055,464 | 10/1991 | Murakami et al. | 514/211 |
| 5,166,151 | 11/1992 | Freidinger et al. | 540/518 |
| 5,206,234 | 4/1993 | Bock et al. | 514/213 |
| 5,220,018 | 6/1993 | Bock et al. | 540/509 |
| 5,302,591 | 4/1994 | Fletcher et al. | 514/221 |
| 5,324,726 | 6/1994 | Bock et al. | 540/221 |
| 5,338,861 | 8/1994 | Botta et al. | 548/552 |
| 5,360,802 | 11/1994 | Chambers et al. | 514/221 |
| 5,410,049 | 4/1995 | Chambers | 540/504 |
| 5,426,185 | 6/1995 | Baldwin et al. | 540/509 |
| 5,428,157 | 6/1995 | Baldwin et al. | 540/509 |
| 5,438,055 | 8/1995 | Baldwin et al. | 514/221 |
| 5,439,905 | 8/1995 | Naka et al. | 514/220 |
| 5,439,906 | 8/1995 | Bock et al. | 514/220 |
| 5,504,077 | 4/1996 | Collins et al. | 540/550 |

FOREIGN PATENT DOCUMENTS

| | | |
|---|---|---|
| 1 190 708 | 7/1985 | Canada . |
| 0 107 095 A1 | 5/1984 | European Pat. Off. . |
| 0 514 133 A1 | 11/1992 | European Pat. Off. . |
| 0 538 945 A1 | 4/1993 | European Pat. Off. . |
| 0 566 175 A2 | 10/1993 | European Pat. Off. . |
| WO 93/02078 | 2/1993 | WIPO . |
| WO 93/08176 | 4/1993 | WIPO . |
| WO 93/15068 | 8/1993 | WIPO . |
| WO 93/07131 | 9/1993 | WIPO . |
| WO 93/17011 | 9/1993 | WIPO . |
| WO 93/19063 | 9/1993 | WIPO . |
| WO 94/05673 | 3/1994 | WIPO . |

OTHER PUBLICATIONS

J. Gen. Physiol., vol. 96, pp. 195–215 (Jul. 1990), by M. C. Sanguinetti, et al.

J. Cardiovasc. Pharmacol., vol. 20, (Suppl. 2) pp. S17–S22 (1992), by L. M. Hondeghem.

*Primary Examiner*—Mark L. Berch
*Attorney, Agent, or Firm*—Elliott Korsen; Mark R. Daniel

[57] ABSTRACT

This invention is concerned with novel compounds represented by structural formula I

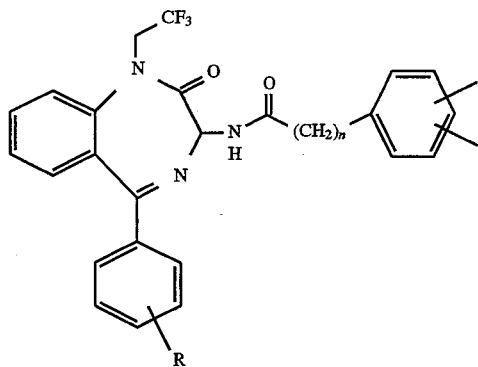

where X and Y are independently hydrogen, chloro, fluoro, bromo, iodo, or trifluoromethyl and n is 0, 1 or 2;

R is hydrogen, fluoro, chloro, bromo, iodo, or trifluoromethyl, methyl, or methoxy; and the racemates, mixtures of enantiomers, individual diastereomers or individual enantiomers with all isomeric forms and pharmaceutically acceptable salts, hydrates or crystal forms thereof, which are antiarrhythmic agents.

10 Claims, No Drawings

2,3-DIHYDRO-1-(2,2,2,-TRIFLUOROETHYL)-2-OXO-5-PHENYL-1H-1,4-BENZODIAZEPINES

CROSS REFERENCE

This is a continuation in part of U.S. patent application Ser. No. 08/292,447 which was filed on Aug. 18, 1994, abandoned.

BACKGROUND OF THE INVENTION

Arrhythmias often occur as complications to cardiac diseases such as myocardial infarction and heart failure. In a serious case, arrhythmias give rise to ventricular fibrillation and can cause sudden death.

Though various antiarrythmic agents are now available on the market, agents exhibiting both satisfactory effects and high safety profiles, have not been obtained. For example, antiarrythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formula I

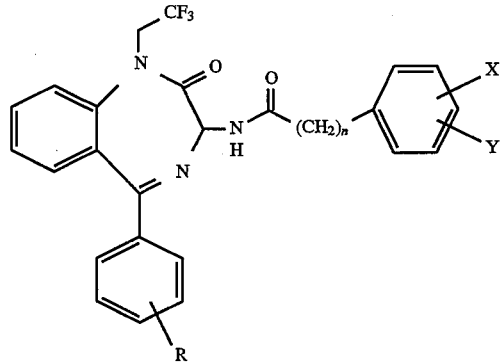

where

X and Y are independently hydrogen, chloro, fluoro, bromo, iodo, or trifluoromethyl and n is 0, 1 or 2;

R is hydrogen, fluoro, chloro, bromo, iodo, or trifluoromethyl, methyl, or methoxy; and the racemates, mixtures of enantiomers, individual diastereomers or individual enantiomers with all isomeric forms and pharmaceutically acceptable salts, hydrates or crystal forms thereof, which are anti-arrhythmic agents. The invention is also concerned with pharmaceutical formulations comprising one of the novel compounds as an active ingredient.

The compounds of the present invention may have asymmetric centers and occur as racemates, mixtures of enantiomers, individual diastereomers, or as individual enantiomers with all isomeric forms being included in the present invention.

The invention is also concerned with a method of treating arrhythmia by the administration of one of the novel compounds or formulation thereof to a patient in need of such treatment.

DETAILED DESCRIPTION OF THE INVENTION

The novel compounds of this invention are represented by structural formula I

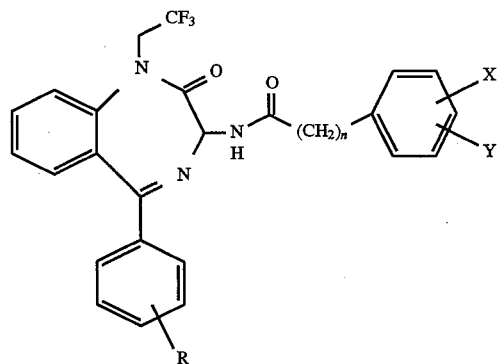

where

X and Y are independently hydrogen, chloro, fluoro, bromo, iodo, or trifluoromethyl and n is 0, 1 or 2;

R is hydrogen, fluoro, chloro, bromo, iodo, or trifluoromethyl, methyl, or methoxy; and the racemates, mixtures of enantiomers, individual diastereomers or individual enantiomers with all isomeric forms and pharmaceutically acceptable salts, hydrates or crystal forms thereof, which are anti-arrhythmic agents. The compounds of the present invention may have asymmetric centers and occur as racemates, mixtures of enantiomers, individual diastereomers, or as individual enantiomers with all isomeric forms being included in the present invention.

The invention is also concerned with a method of treating arrhythmia by the administration of one of the novel compounds or formulation thereof to a patient in need of such treatment.

The most preferred embodiment of this invention is (−)-2-[2,4-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide.

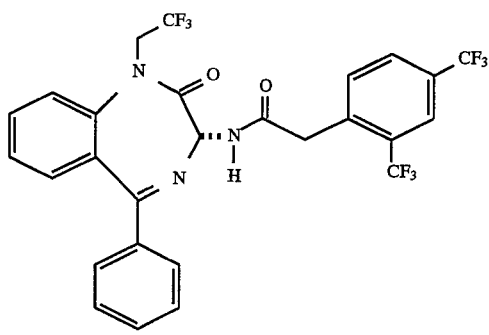

Another embodiment of the novel compounds of this invention is (+)-3,5-Dichloro-N-[3R-2,3-dihydro-2-oxo-5-phenyl-1-(2,2,2-trifluoroethyl)-1H-benzo[e][1,4]diazepin-3-yl]benzamide.

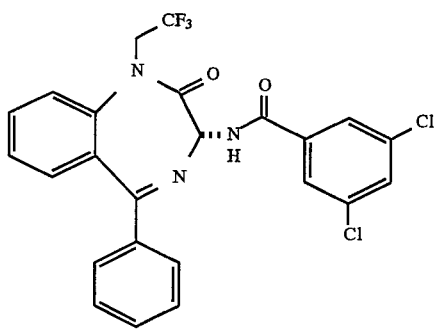

An additional embodiment of the novel compounds of this invention is (−)-2-(3,4-Dichlorophenyl)-N-[3R-2,3-dihydro-2-oxo-5-phenyl-1-(2,2,2-trifluoroethyl)-1H-benzo[e][1,4]diazepin-3-yl]acetamide.

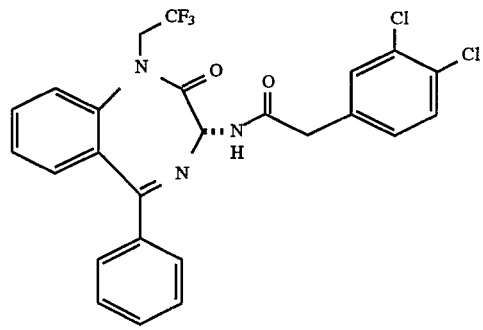

Still another embodiment of the novel compounds of this invention is (−)-2-(3,5-Dichlorophenyl)-N-[3R-2,3-dihydro-2-oxo-5-phenyl-1-(2,2,2-trifluoroethyl)-1H-benzo[e][1,4]diazepin-3-yl]acetamide.

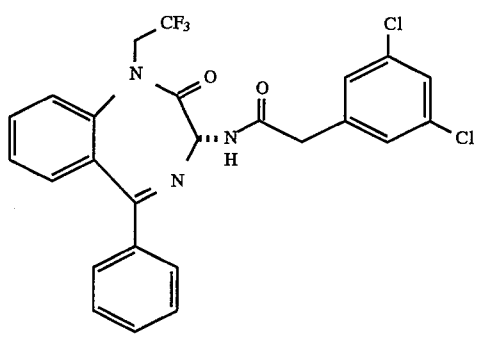

Other examples of embodiments of this invention are:
3-Cyclohexyl-N-[5-(2-fluorophenyl)-2-oxo-1-(2,2,2-trifluoroethyl-2,3-dihydro-1H-benzo[e][1,4]diazepin-3-yl] propionamide.

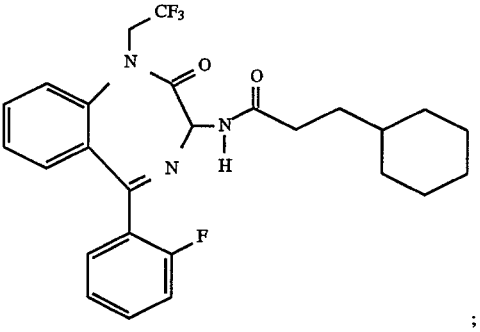

3,4-Dichloro-N-[5-(2-fluorophenyl)2-oxo-1-(2,2,2-trifluoroethyl)-2,3-dihydro-1H-benzo[e][1,4]diazepin-3-yl] benzamide.

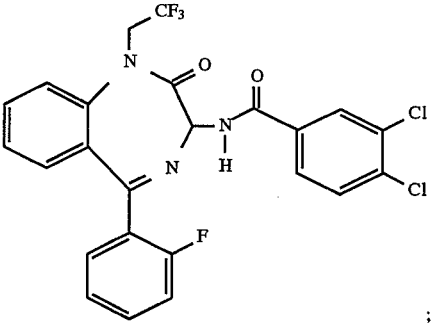

(−)-2-[3,5-Bis(trifluoromethyl)phenyl]-N-[3R-2,3-dihydro-2-oxo-5-phenyl-1-(2,2,2-trifluoroethyl)-1H-benzo[e][1,4] diazepin-3-yl]acetamide.

5                                                          6

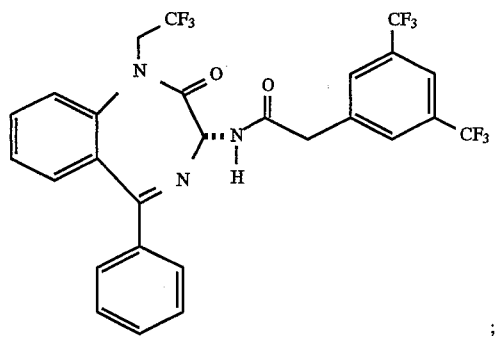

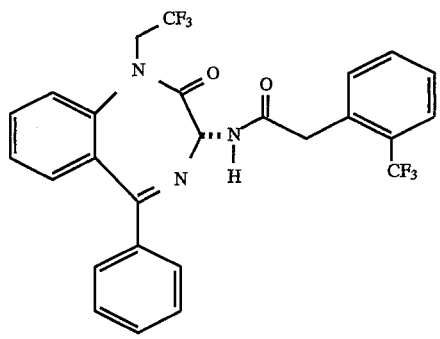

(−)-2-(4-Trifluoromethylphenyl)-N-[3R-2,3-dihydro-2-oxo-5-phenyl-1-(2,2,2-trifluoroethyl)-1H-benzo[e][1,4]diazepin-3-yl]acetamide (−)-2-(2,4-Dichlorophenyl)-N-[3R-2,3-dihydro-2-oxo-5-phenyl-1-(2,2,2-trifluoroethyl)-1H-benzo[e][1,4]diazepin-3-yl]acetamide

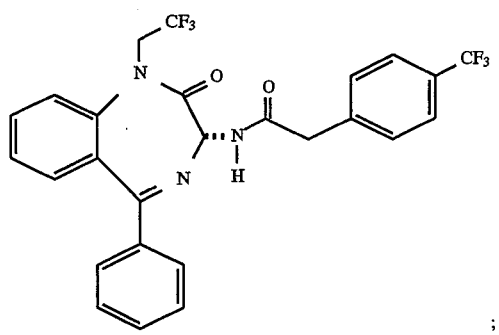

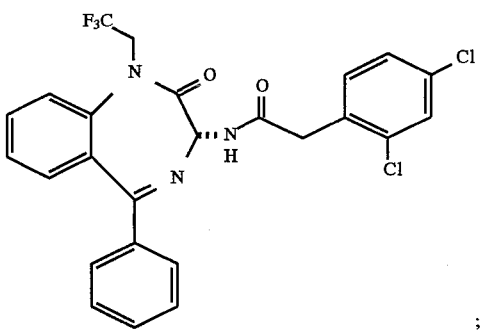

(−)-2-(3-Trifluoromethylphenyl)-N-[3R-2,3-dihydro-2-oxo-5-phenyl-1-(2,2,2-trifluoroethyl)-1H-benzo[e][1,4]diazepin-3-yl]acetamide (−)-2-(3-Chlorophenyl)-N-[3R-2,3-dihydro-2-oxo-5-phenyl-1-(2,2,2-trifluoroethyl)-1H-benzo[e][1,4]diazepin-3-yl]acetamide

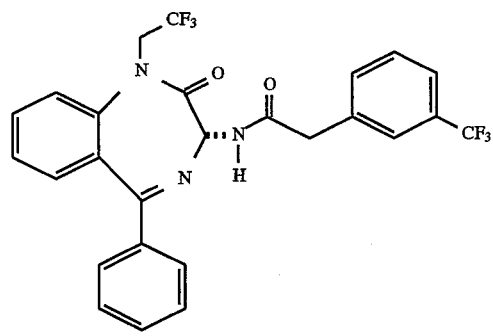

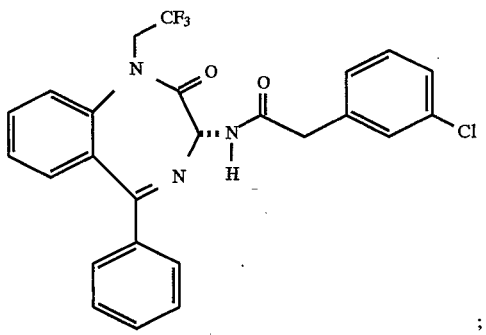

(−)-2-(2-Trifluoromethylphenyl)-N-[3R-2,3-dihydro-2-oxo-5-phenyl-1-(2,2,2-trifluoroethyl)-1H-benzo[e][1,4]diazepin-3-yl]acetamide (−)-2-(4-Chlorophenyl)-N-[3R-2,3-dihydro-2-oxo-5-phenyl-1-(2,2,2-trifluoroethyl)-1H-benzo[e][1,4]diazepin-3-yl]acetamide

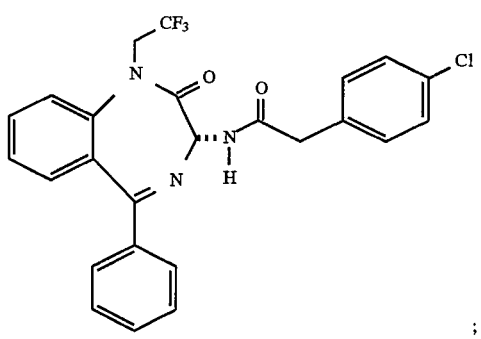

(+)-2-(3,5-Dichlorophenyl)-N-[2,3-dihydro-2-oxo-5-(4-fluorophenyl)-1-(2,2,2-trifluoroethyl)-1H-benzo[e][1,4]diazepin-3-yl]acetamide

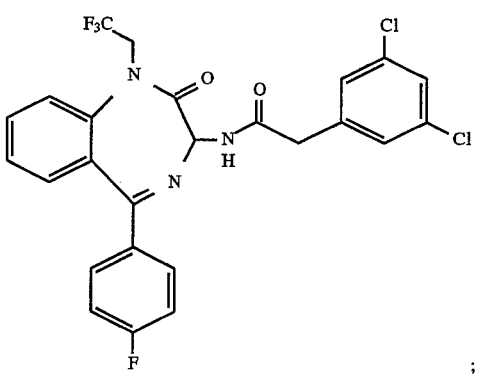

(−)-2-(2,4-Dichlorophenyl)-N-[2-oxo-5-(4-fluorophenyl)-1-(2,2,2-trifluoroethyl)-2,3-dihydro-1H-benzo[e][1,4]diazepin-3-yl]acetamide

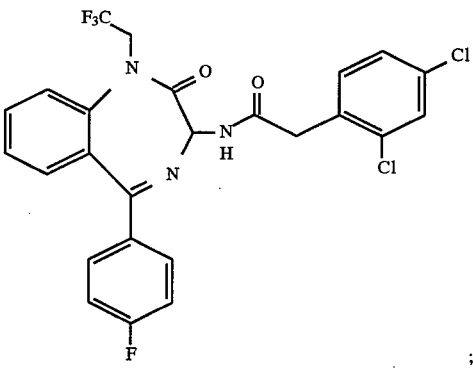

(+)-2-[3,5-Bis(trifluoromethyl)phenyl]-N-[2-oxo-5-(4-fluorophenyl)-1-(2,2,2-trifluoroethyl)-2,3-dihydro-1H-benzo[e][1,4]diazepin-3-yl]-acetamide

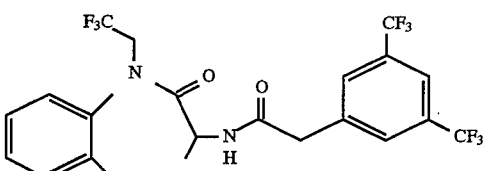

(−)-2-[2,4-Bis(trifluoromethyl)phenyl]-N-[2-oxo-5-(4-fluorophenyl)-1-(2,2,2-trifluoroethyl)-2,3-dihydro-1H-benzo[e][1,4]diazepin-3-yl]-acetamide

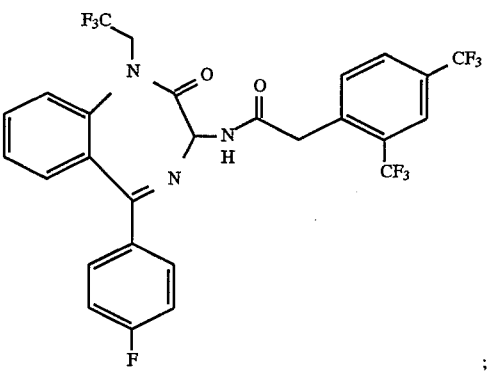

2-(3,5-Dichlorophenyl)-N-[2,3-dihydro-2-oxo-5-phenyl-1-(2,2,2-trifluoroethyl)-1H-benzo[e][1,4]diazepin-3-yl]acetamide

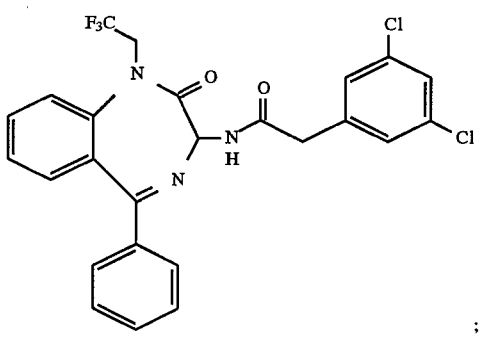

A novel process for preparing the compounds of this invention is schematically exemplified below in Scheme I, and these steps are well known in the art and/or described in the Examples that follow.

Scheme 1
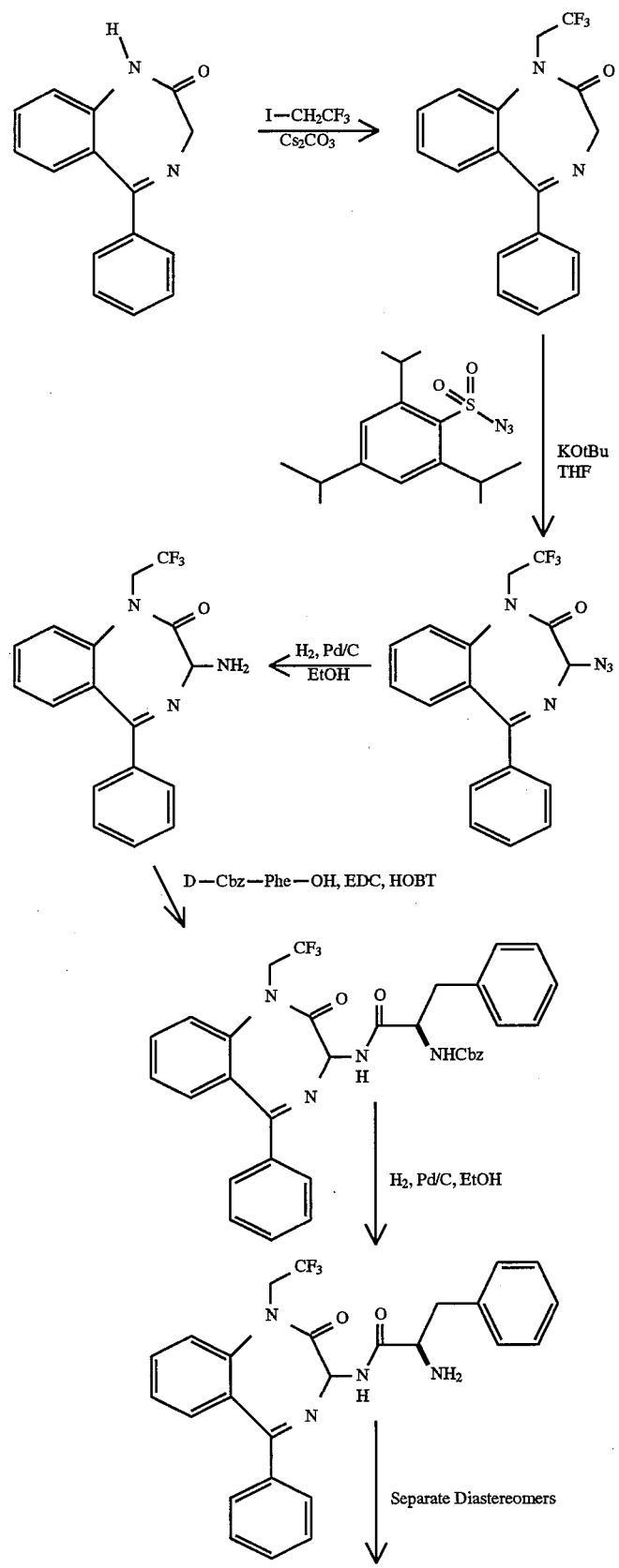

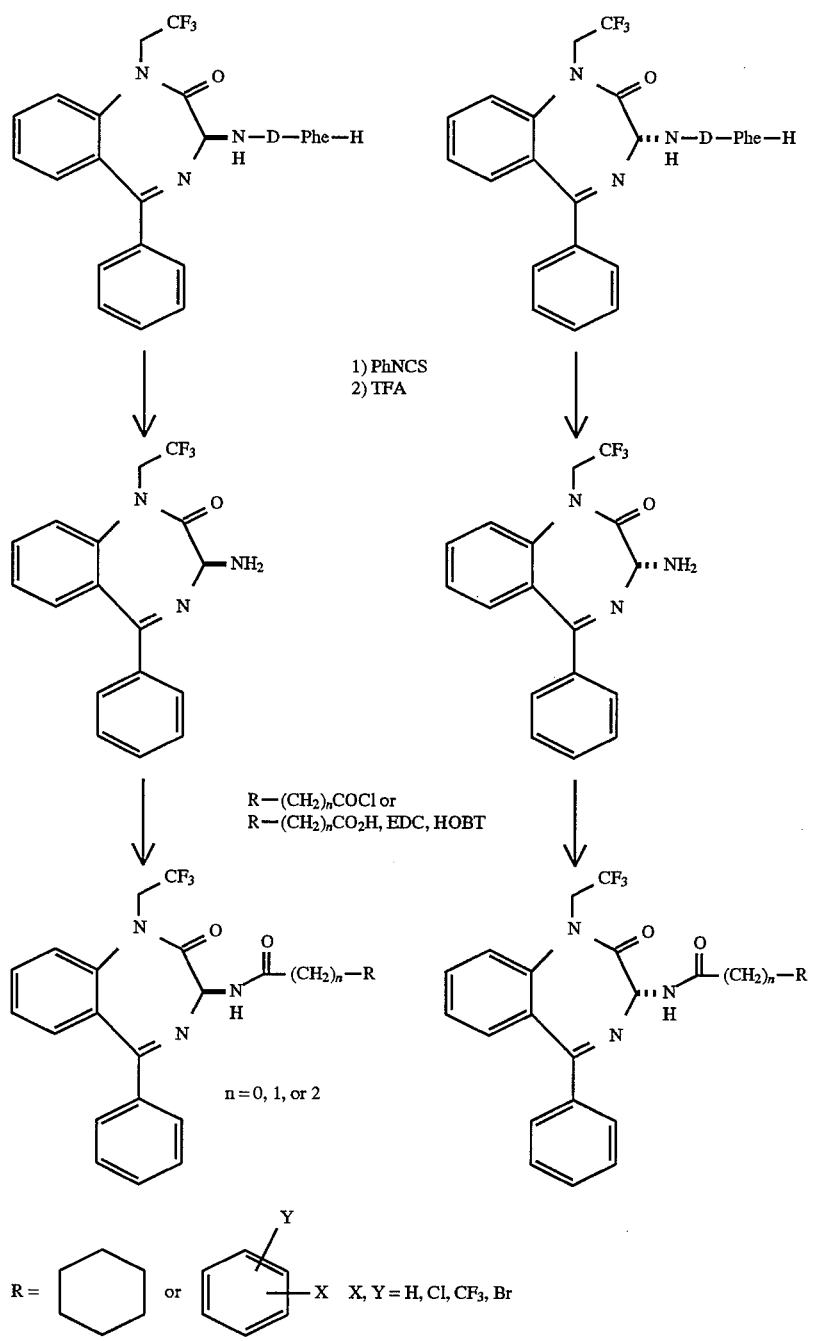

-continued
Scheme 1

The novel compounds of the present invention have the pharmacological properties required for antiarrhythmic agents of Class III, namely they demonstrate prolongation of QTc-interval, and dose dependent increases in ventricular refractoriness. This is accomplished without effecting heart rate, mean arterial pressure and PR and QRS intervals. Modest increases in LV+dP/dt (left ventricular change in pressure with time) is observed. Further, these compounds suppress the induction of PVS (Programmed Ventricular Stimulation) induced ventricular tachyarrhythmias.

These compounds are effective in treating and preventing all types of arrhythmias including ventricular and atrial (supraventricular) arrhythmias. The compounds of the present invention are especially useful for controlling reentrant arrhythmias and prevent sudden death due to ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 10 mg per kg of body weight per day, preferably from about 0.0001 to about 2 mg per kg of body weight per day, and more preferably by intravenous delivery of from about 0.0003 to about 0.3 mg per kg of body weight per day, or when given orally from about 0.03 to about 1 mg per kg of body weight per day, in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II, or Class IV antiarhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrate. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as antiarrhythmic agents is measured by their ability to block the $I_{Ks}$ and $I_{Kr}$ currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K$^+$ current: differential sensitivity to block by Class III antiarrhythmic agents. J. Gen. Physiol. 96:195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4KCl, 1.2 MgCl$_2$, 10 HEPES, 10 glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). $I_{Kr}$ is measured as peak outward current during the voltage ramp. $I_{Kr}$ is measured as tail currents upon repolarization from −10 mV to −50 mV. $I_{Ks}$ is measured as time-dependent current during the pulse to +50 mV. Currents are measured during control, then after exposure to drug at two different concentrations.

Employing this test the compounds described herein have an IC$_{50}$ of less then 100 nM as $I_{Ks}$ blockers. The compounds of this invention are at least 10 times more potent in the blockade of $I_{Ks}$ than of blockade of $I_{Kr}$.

EXAMPLES

Example 1

(+)-3,5-Dichloro-N-[3R2,3-dihydro-2-oxo-5-phenyl-1-(2,2,2-trifluoroethyl)-1H-benzo[e][1,4]diazepin-3-yl]benzamide.

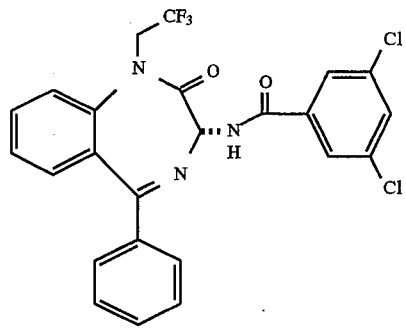

Step A:

Preparation of 2,3-dihydro-2-oxo-5-phenyl-1-(2,2,2-trifluoroethyl)-1H-benzo[e][1,4]diazepine A solution of 5-phenyl-1,4-benzodiazepine-2-one (J. Org. Chem., 1962, 27, 3788)(50 g, 0.211 mole) in DMF (100 mL) was treated with cesium carbonate (103.5 g, 0.317 mole) and trifluoroethyl iodide.(109.7 g, 0.525 mole). The mixture was stirred at 50° C. overnight. The reaction mixture was then poured into water (2 L) and extracted with ethyl acetate (3×1 L). The combined ethyl acetate fractions were dried over anhydrous magnesium surf ate, filtered and concentrated at reduced pressure. The residue was crystallized from ethyl ether to give 45 g (68%) of the product. MP=130°–131° C.;

$^1$H NMR (CDCl$_3$, 300 MHz) δ7.65–7.60 (m, 2H), 7.60–7.45 (m, 5H), 7.40–7.20(m, 2H), 5.25 (dq, J=14, 8.6 Hz, 1H), 4.82(d, J=10.5 Hz, 1H), 4.15 (app sextet, J=8.6 Hz, 1H), 3.81 (d, J=10.5 Hz, 1H)

Step B:

Preparation of 3-Azido-5-phenyl-1-(2,2,2-trifluoroethyl)-1H-benzo[e][1,4]diazepine To a stirring solution of 5-phenyl-1-(2,2,2-trifluoroethyl)-1H-benzo[e][1,4]diazepine (70 g,0.22 mol) in THF (1500 mL) cooled to −70° C. was added potassium tert-butoxide (1.1 eq, 0.24 mol, 240 mL of a 1N solution in THF) dropwise over 15 min. A solution of 2,4,6-triisopropylbenezenesulfonylazide (74.8 g, 0.24 mol) in THF (250 ml) was added over 5 min. This was stirred for 10 minutes and acetic acid (40 mL, 0.63 mol) was added and the reaction allowed to warm to ambient temperature. The reaction was poured into satd. NaHCO₃ (1500 mL) and ethyl acetate (1 L). The phases were separated and the aqueous phase was extracted with ethyl acetate(500 mL). The combined organic layers were washed with water (500 mL) then brine (300 mL). The organic layers were dried with Na₂SO₄ and evaporated to a brown foam. This was triturated with ethyl ether to give 65 g of a white powder. The filtrate was concentrated and chromatographed over silica gel eluting with 30% ethyl acetate/hexane to give another 8.9 g. The combined yield was 74 g(93%). MP=159°–160° C.;

¹H NMR (CDCl₃, 300 MHz) δ7.70–7.26 (m,9H), 5.28–5.12 (m,1H), 4.63 (s,1H), 4.35–4.10 (m,1H).

Step C:

Preparation of racemic 3-Amino-5-phenyl-1-(2,2,2-trifluoroethyl)-1H-benzo[e][1,4]diazepine To a stirring solution of 3-Azido-2-oxo-5-phenyl-1-(2,2,2-trifluoroethyl)-2,3-dihydro-1H-benzo[e][1,4]diazepine (83.4 mmol ,30 g) in 300 mL ethanol and 150 mL THF was added 10% Pd/C (10 wt %, 3.0 g). Hydrogen gas was bubbled through the solution for 8 h. The reaction was filtered and evaporated under reduced pressure. The residue was crystallized from ethyl ether to give 20.0 g of white crystals. Another 4 g was recovered from evaporation and recrystallization of the filtrates. Combined yield, 86.7%.

MP=141°–143° C.;

¹H NMR (CDCl₃,300 MHz) δ7.70–7.26 (m,9H), 5.28–5.12 (m,1H), 4.57 (s,1H), 4.35–4.10 (m,1H).

Step D:

Preparation of 2-Amino-N-[2-oxo-5-phenyl-1-(2,2,2-trifluoroethyl)-2,3-dihydro-1H-benzo[e][1,4]diazepin-3-yl]-3-phenylpropionamide To a stirring solution of 3-Amino-2-oxo-5-phenyl-1-(2,2,2-trifluoroethyl)-2,3-dihydro-1H-benzo[e][1,4]diazepine (92.2 mmol, 30.74 g) in DMF (300 mL) was added N-Benzyloxy-D-Phenyl-alanine (92.2 mmol, 27.6 g), 1-(3-Dimethylaminopropyl)-3-ethylcarbodiimide hydrochloride (0.12 mol, 22.95 g) and 1-hydroxybenztriazole hydrate (46.1 mmol, 6.23 g). This was stirred at room temperature for 2 h. The reaction was then diluted with 1 L of 10% KHSO₄ and extracted with ethyl acetate (2×600 mL). The organic layers were combined and washed with saturated sodium hydrogen carbonate (600 mL). They were dried with brine and sodium surf ate and evaporated under reduced pressure. 66.58 g of an orange foam, which contained ethyl acetate by NMR. NMR ¹H (CDCl₃) δ7.75–7.18 (m, 20H), 5.62–5.55 (m, 1H), 5.48–5.00 (m, 4H), 4.72–4.60 (m, 1H), 4.25–4.05 (m, 1H) 3.32–3.05 (m, 2H). This material was carried on without further purification. To a stirring solution of 2-(N-Benzyloxyamino)-N-[2-oxo-5-phenyl-1-(2,2,2-trifluoroethyl)-2,3-dihydro-1H-benzo[e][1,4]diazepin-3-yl]-3-phenyl propionamide in 1 L ethanol was added 10% Pd/C (15 wt %) and hydrogen was bubbled through the reaction for 2 h and then left stirring under 1 atm. hydrogen overnight. Hydrogen was bubbled through the reaction for an additional three hours the following morning. The reaction was then filtered, the catalyst was rinsed with 1 L methylene chloride and evaporated under reduced pressure. The resulting solid was dried under vacuum overnight to give 44.46 g of a white solid. This was chomatographed over silica, eluting with 1% MeOH:EtOAc. The pure upper R_f fractions were collected and evaporated under reduced pressure. The mixed fractions were collected, evaporated and rechromatographed. The pure fractions were collected and combined with the above pure fractions to get a combined yield of 18.11 g, 83.5% of the upper Rf diastereomer. ¹H NMR (CDCl₁₃,300 MHz) δ8.94 (d, J=8.6 Hz, 1H), 7.65–7.10 (m, 9H), 5.64 (d, J=8.6 Hz, 1H), 5.28–5.12 (m, 1H), 4.57 (s, 1H), 4.35–4.10 (m, 1H) 3.71 (dd, J=9.8 and 3.9 Hz, 1H), 3.34 (dd, J=13.9 and 3.9 Hz,1H), 2.79 (dd, J=13.9 and 10.0 Hz, 1H). The Absolute stereochemistry at C-3 of the benzodiazepine ting was determined to be (R) by X-Ray analysis. The lower Rf material corresponding to C-3(S) was isolated as well.

Step E:

Preparation of 3(R)-(+)-3-Amino-5-phenyl-1-(2,2,2-trifluoroethyl)-1H-benzo[e][1,4]diazepine To a stirring solution of 2-Amino-N-[2-oxo-5-phenyl-1-(2,2,2-trifluoroethyl)-2,3-dihydro-1H-benzo[e][1,4]diazepin-3-yl]-3-phenylpropionamide (13.6 g, 28.3 mmol) in methylene chloride (136 mL) was added phenyl isothiocynate (3.87 mL, 34.0 mmol). This was stirred overnight at ambient temperature. The reaction was then cooled in ice, trifluoroacetic acid (2.73 mL, 0.283 mol) added and the reaction allowed to warm to ambient temperature. After stirring at ambient temperature for 2.5 hours the reaction was evaporated under reduced pressure, chromatographed with 90:10:1:1 methylene chloride:methanol: acetic acid::water. The low R_f spot was collected and evaporated under reduced pressure with no heat. The residue was taken up in 600 mL methylene chloride and washed with 300 mL saturated NaHCO₃ and 300 mL water. The solution was dried over Na₂SO₄ and evaporated under reduced pressure. The residue was crystallized from ethyl acetate:hexanes to give 6.65 g of a white powder. MP=162°–164° C.;

¹H NMR (CDCl₃,300 MHz) δ7.70–7.26 (m,9H), 5.28–5.12 (m,1H), 4.57 (s,1H), 4.35–4.10 (m,1H).

[α]D=+72.9° (c=0.7, MeOH)

The (−)-3S enantiomer was prepared in the same fashion from the Lower Rf product of Step D.

MP=156°–158° C.;

¹H NMR (CDCl₃,300 MHz) δ7.70–7.26 (m,9H), 5.28–5.12 (m,1H), 4.57 (s,1H), 4.35–4.10 (m,1H).

[α]_D=−71.2° (c=0.66, MeOH)

Step F:

Preparation of (+)-3,5-Dichloro-N-[3R-2,3-dihydro-2-oxo-5-phenyl-1-(2,2,2-trifluoroethyl)-1H-benzo[e][1,4]diazepin-3-yl]benzamide To a stirring solution of (+)-3R-3-amino-5-phenyl-1-(2,2,2-trifluoroethyl)-1H-benzo[e][1,4]diazepine (5.6 g, 16.8 mmol) in DMF (50 mL) was added 1-(3Dimethylaminopropyl-3-ethylcarbodiimide hydrochloride(4.44 g, 23.0 mmol), and 1-hydroxybenztriazole hydrate (3.11 g, 23.0 mmol) and 3,5-Dichlorobenzoic acid (3.21 g, 16.8 mmol). This was stirred at ambient temperature for 2 hours. The reaction was diluted with 500 mL satd. NaHCO₃ and extracted with 2×300 mL ethyl acetate. The combined organics were washed with 10% KHSO₄ (200 mL), brine (200 mL), dried over Na₂SO₄, and evaporated to a white foam. This was chromatographed over a 75×200 mm silica column eluting with 20% ethyl acetate:hexane. The pure fractions were collected and evaporated under reduced pressure to give 8.5 g of a white foam which was crystallized from 15% ethyl acetate:hexane to give 5.3 g of a white powder. mp=140°–143° C., [α]_D=+47.9°; ¹H NMR (CDCl₃, 300 MHz) δ7.85–7.75 (m, 2H), 7.70–7.20 (m, 9H), 5.78 (d, J=8.1 Hz,1H), 5.30–5.15 (m, 1H), 4.30–4.15 (m, 1H)

Analysis Calcd. for C₂₄H₁₆Cl₂F₃N₃O₂: C, 56.93; H, 3.19; N, 8.30; Found: C, 56.81; H, 3.17; N, 8.17.

The following examples were prepared by a procedure substantially as described for Example 1, Step F.

Example 2

(−)-2-(3,4-Dichlorophenyl)-N-[3R-2,3-dihydro-2-oxo-5-phenyl-1-(2,2,2-trifluoroethyl)-1H-benzo[e][1,4]diazepin-3-yl]acetamide.

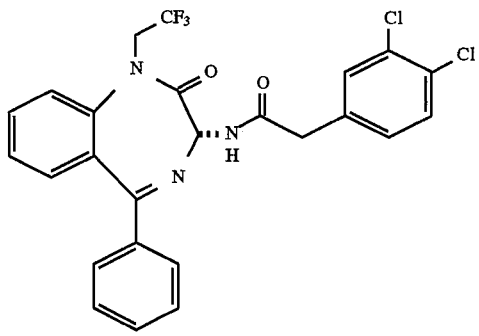

mp=219°–221° C.; [αz]$_D$=−10.8°;

$^1$H NMR (CDCl$_3$,300 MHz) δ7.65–7.15 (m, 12H), 5.78 (d, J=8.1 Hz, 1H), 5.25–5.10 (m, 1H), 4.25–4.05 (m, 1H), 3.56 (s, 2H);

Analysis Calcd. for C$_{25}$H$_{18}$Cl$_2$F$_3$N$_3$O$_2$. 0.85 H$_2$O: C, 56.06; H, 3.71; N, 7.84. Found: C, 56.03; H, 3.53; N, 7.82.

Example 3

(−)-2-(3,5-Dichlorophenyl)-N-[3R-2,3-dihydro-2-oxo-5-phenyl-1-(2,2,2-trifluoroethyl)-1H-benzo[e][1,4]diazepin-3-yl]acetamide

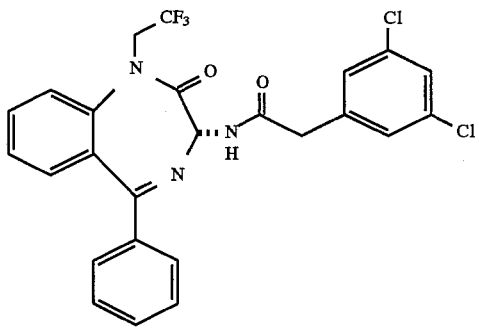

mp=93°–100° C., [α]$_D$=−5.7°;

$^1$H NMR (CDCl$_3$,300 MHz) δ7.65–7.15 (m, 12H), 5.78 (d, J=8.1 Hz, 1H), 5.25–5.10 (m, 1H), 4.25–4.05 (m, 1H), 3.65 (s, 2H);

Analysis Calcd. for C$_{25}$H$_{18}$Cl$_2$F$_3$N$_3$O$_2$: C, 57.71; H, 3.49; N, 8.08; Found: C, 57.41; H, 3.48; N, 8.12,

Example 4

(−)-2-[3,5Bis(trifluoromethyl)phenyl]N-[3R-2,3-dihydro-2oxo-5-phenyl-1-(2,2,2-trifluoroethyl)-1H-benzo[e][1,4]diazepin-3-yl]acetamide

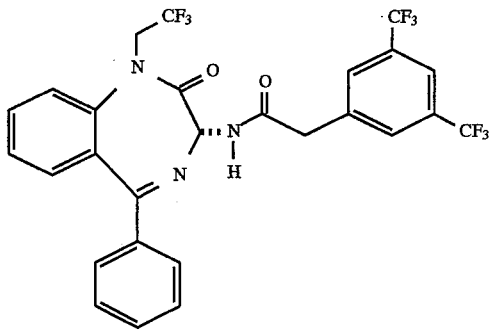

m.p. foam ° C., [α]$_D$=−9.7° (c=0.59,MeOH).

Anal. Calcd. for C$_{27}$H$_{18}$F$_9$N$_3$O$_2$.0.75 H$_2$O: C, 53.96; H, 3.27; N, 6.99. Found: C, 53.96; H, 3.; N, 6.98%.

Example 5

(−)-2-(4-Trifluoromethylphenyl)-N-[3R-2,3-dihydro-2-oxo-5-phenyl-1-(2,2,2-trifluoroethyl)-1H-benzo[e][1,4]diazepin-3-yl]acetamide

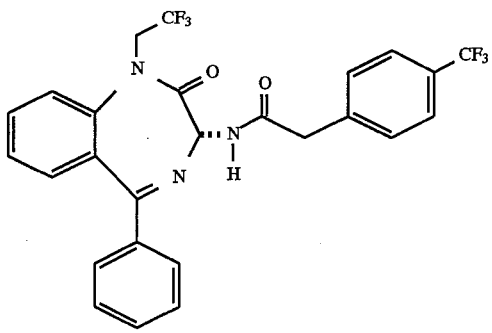

m.p. 253°–255° C., [α]$_D$=−9.2° (c=0.25, MeOH).

Anal. Calcd. for C$_{26}$H$_{19}$F$_6$N$_3$O$_2$.0.05 ethyl ether 0.55 H2O: C, 59,03; H, 3.9; N, 7.88. Found: C, 59.05; H, 3.82; N, 7.78%.

Example 6

2-(3-Trifluoromethylphenyl)-N-[3R-2,3-dihydro-2-oxo-5-phenyl-1-(2,2,2-trifluoroethyl)-1H-benzo[e][1,4]diazepin-3-yl]acetamide

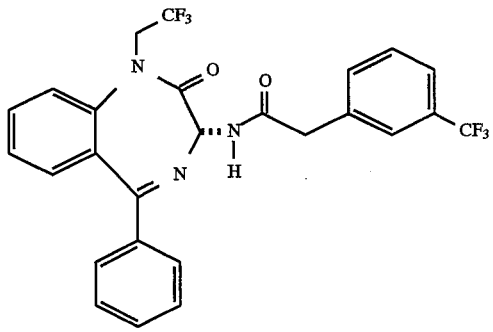

m.p. 172°–173° C., [α]$_D$=+5.9° (c=0.56, CHCl3).

Anal. Calcd. for C$_{26}$H$_{19}$F$_6$N$_3$O$_2$.0.60 H2O: C, 58.89; H, 3.84; N, 7.92. Found: C, 58.92; H, 3.71; N, 7.98%.

Example 7

(+)-2-(2-Trifluoromethylphenyl)-N-[3R-2,3-dihydro-2-oxo-5-phenyl-1-(2,2,2-trifluoroethyl)-1H-benzo [e][1,4]diazepin-3-yl]acetamide

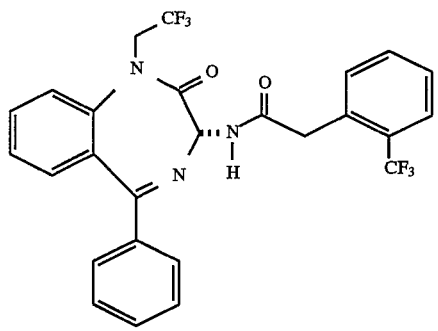

m.p. 170°–171° C., $[\alpha]_D$=+9.0° (c=0.48, CHCl3).

Anal. Calcd. for $C_{26}H_{19}F_6N_3O_2 \cdot 0.25\ H_2O$: C, 59.6; H, 3.75; N, 8.02. Found: C, 59.64; H, 3.68; N, 7.97%.

Example 8

(−)-2-(2,4-Dichlorophenyl)-N-[3R-2,3-dihydro-2-oxo-5-phenyl-1-(2,2,2-trifluoroethyl)-1H-benzo [e][1,4]diazepin-3-yl]acetamide

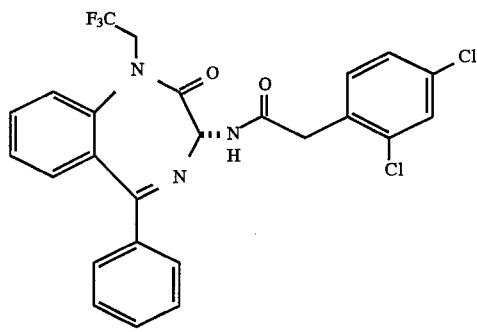

m.p. 143°–145° C., $[\alpha]_D$=−22.6° (c=0.73; MeOH).

Anal. Calcd. for $C_{25}H_{18}N_3O_2Cl_2F_3$: C, 57.71; H, 3.49; N, 8.08. Found: C, 57.75; H, 3.52; N, 8.09%.

Example 9

(−)-2-(3-Chlorophenyl)-N-[3R-2,3-dihydro-2-oxo-5-phenyl-1-(2,2,2-trifluoroethyl)-1H-benzo[e][1,4]diazepin-3-yl]acetamide

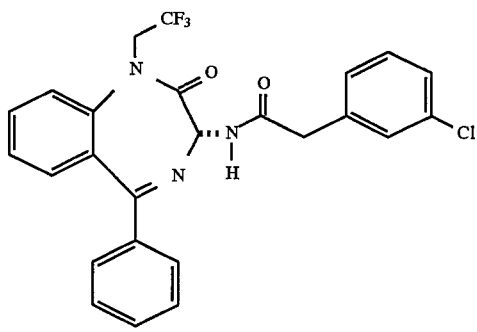

m.p. 188°–189° C., $[\alpha]_D$=−5.4° (c=1.03,MeOH).

Anal. Calcd. for $C_{25}H_{19}ClF_3N_3O_2 \cdot 0.10$ ethyl ether: C, 61.84; H, 4.09; N, 8.52. Found: C, 61.84; H, 4.05; N, 8.5%.

Example 10

(−)-2-(4-Chlorophenyl)-N-[3R-2,3-dihydro-2-oxo-5-phenyl-1-(2,2,2-trifluoroethyl)-1H-benzo[e][1,4]diazepin-3-yl]acetamide

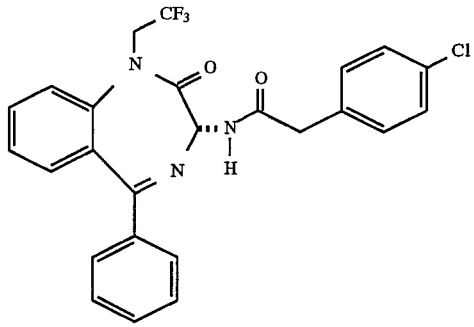

m.p. 246°–247° C., $[\alpha_D]D$=−10.1° (c=0.45,MeOH).

Anal. Calcd. for $C_{25}H_{19}ClF_3N_3O_2 \cdot 0.15$ ethyl ether: C, 61.42; H, 4.21; N, 8.39. Found: C, 61.46; H, 4.15; N, 8.39%.

Example 11

(−)-2-[2,4-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide

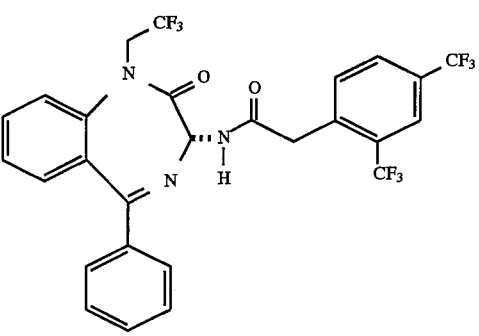

Step A.:

2,4-Bis(trifluoromethyl)benzonitrile

To a stirring biphasic mixture of 100 mL ethanol and 250 mL of phosphate buffer (1 g of $NaH_2PO_4 \cdot H_2O$ per 5 mL $H_2O$ adjusted to pH=7.0 with 50% NaOH) and NaCN (81.3 mmol,4.0 g) heated to 60° C. was added 2,4-bis (trifluoromethyl) benzyl bromide (32.5 mmol, 10 g) in 50 mL EtOH dropwise over 30 min. The reaction was heated at 60° C. for 24 h. The reaction was then evaporated under reduced pressure. The remaining aqueous was extracted with 2×150 mL EtOAc. The organic layers were combined, dried with brine and $Na_2SO_4$. The organic phase was evaporated under reduced pressure and the residue chromatographed over silica eluting with 10% EtOAc:Hexanes. The pure fractions were collected and evaporated to give 7.0 g of a pale yellow oil, 85.1% NMR $^1H$ (CDCl$_3$) δ8.0–7.85 (m,3H), 4.03 (s,2H)

Step B:

2,4-Bis(trifluoromethyl)phenyl acetic acid 2,4-Bis(trifluoromethyl)benzonitrile (41.5 mmol, 10.51 g) was taken up in 100 mL acetic acid, 50 mL conc. $H_2SO_4$, and 20 mL water. This was heated to 120° C. for 3 h. The reaction was then diluted with 1 L ice water, and extracted with 2×300 mL ethyl acetate. The combined organics were washed with 2×200 mL water, dried with brine and Na$_2$SO$_4$, and evaporated under reduced pressure. The residue was taken up in a minimum of diethyl ether and crystallized by adding sufficient hexane to precipatate the product. The solid was collected to give 7.74 g of 2,4-bis(trifluoromethyl) phenyl acetic acid as white crystals, 68.5%. NMR $^1$H (CDCl$_3$) δ7.93 (s,1H), 7.80 (d, J=7.9 Hz,1H), 7.55 (d, J=7.9 Hz,1H), 3.94 (s,2H).

Step C:

Preparation of (−)-2-[2,4-Bis(trifluoromethyl) phenyl]-N-[3R-2,3-dihydro-2-oxo-5-phenyl-1-(2,2, 2trifluoroethyl)-1H-benzo[e][1,4]diazepin-3-yl] acetamide To a stirring solution the 3R-3-Amino-2-oxo-5-phenyl-1-(2,2,2-trifluoroethyl)-2,3-dihydro -1H-benzo[e][1,4]diazepine (28.4 mmol, 9.47 g) in DMF (100 mL) was added 2,4-Bis(trifluoromethyl)phenyl acetic acid (28.4 mmol,7.74 g), 1-(3-Dimethylaminopropyl)-3-ethylcarbodiimide hydrochloride (42.6 mmol, 8.16 g) and 1-Hydroxybenztriazole hydrate (14.2 mmol,1.92 g). This was stirred for 1 h at room temperature. The reaction was then diluted with 750 mL of 10% KHSO$_4$ and extracted with ethyl acetate (2×300 mL). The organic layers were combined and washed with saturated sodium hydrogen carbonate (1×600 mL). The organics were then dried with brine, and sodium sulfate and evaporated under reduced pressure. The residue was chromatographed over silica eluting with 20% EtOAc:Hexane. Pure fractions were collected and evaporated. The residue was taken up in 100 mL of warm 75% isopropanol:water. This was allowed to cool slowly and stirred overnight (16 hr) at room temperature. The suspension was cooled briefly to @5° C. and filtered. The white solid was dried overnight at 60° C. to give 10.5 g of material that melted at 132°–134° C. X-Ray diffraction confirms crystallinity. NMR $^1$H (CDCl$_3$) 7.95–7.25 (m, 13H), 5.60 (d,J=8.1 Hz, 1H), 5.30–5.10 (m,1H), 4.25–4.06 (m, 1H), 3.96 (s,2H)

Anal. Calcd. for C$_{27}$H$_{18}$F$_9$N$_3$O$_2$: C, 55.20; H, 3.09; N, 7.15. Found: C, 55.03; H, 3.14; N, 7.10%.

Example 12

(±)-2-(3,5-Dichlorophenyl)-N-[2,3-dihydro-2-oxo-5-phenyl-1-(2,2,2-trifluoroethyl)-1H-benzo[e][1,4]diazepin-3-yl]acetamide

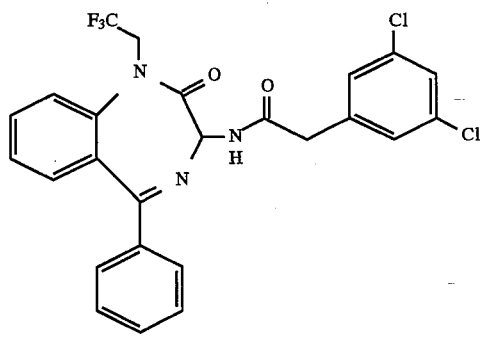

m.p. 219°–220 ° C. racemic

Anal. Calcd. for C$_{25}$H$_{18}$N$_3$O$_2$Cl$_2$F$_3$: C, 57.71; H, 3.49; N, 8.08. Found: C, 57.94; H, 3.48; N, 8.02%.

Example 13

2-(3,5-dichloro-4-methoxyphenyl)-N-[3R-2,3-dihydro-2-oxo-5-phenyl-1-(2,2,2-trifluoroethyl)-1H-benzo[e][1,4] diazepin-3-yl]acetamide

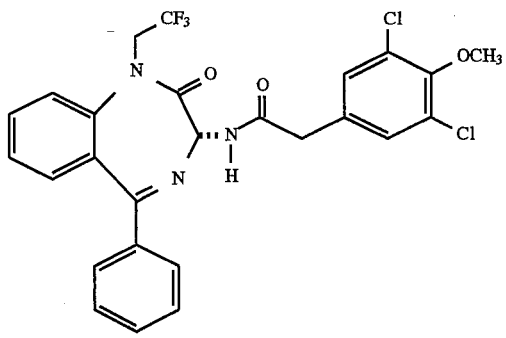

m.p. 100°–104° C., [α]$_D$=−8.9° (c=0.55,MeOH).

Anal. Calcd. for C$_{26}$H$_{20}$Cl$_2$F$_3$N$_3$O$_3$: C, 56.74; H, 3.66; N, 7.63. Found: C, 55.67; H, 3.47; N, 7.41%.

The following examples were prepared by procedures substantially as described in example 1 except substituting the appropriate fluoro substituted aminobenzophenone in step A.

Example 14

(+)-2-(3,5-Dichlorophenyl)-N-[2,3-dihydro-5-(4-fluorophenyl)-2-oxo-1-(2,2,2trifluoroethyl)-1H-benzo[e][1, 4]diazepin-3-yl]acetamide

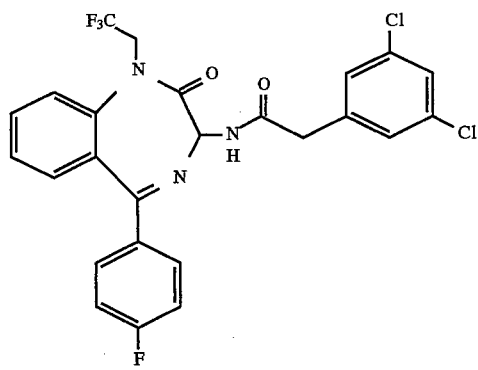

m.p. foam ° C., [α]$_D$=+3.4° (c=0.55; MeOH).

Anal. Calcd. for C$_{25}$H$_{17}$N$_3$O$_2$Cl$_2$F$_4$: C, 55.78; H, 3.18; N, 7.81. Found: C, 55.73; H, 3.25; N, 7.72%.

Example 15

(−)-2-(2,4-Dichlorophenyl)-N-[2,3-dihydro-5-(4-fluorophenyl)-2-oxo-1-(2,2,2-trifluoroethyl)-1H-benzo[e] [1,4]diazepin-3-yl]acetamide

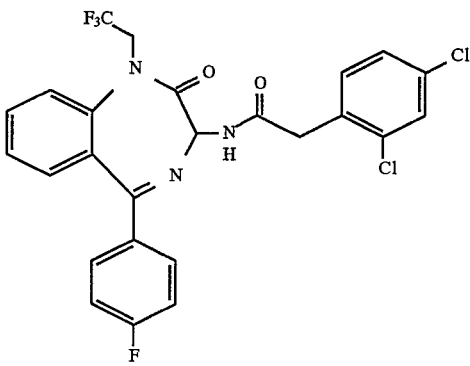

m.p. foam ° C., [α]$_D$=–11° (c=0.68; MeOH).

Anal. Calcd. for $C_{25}H_{17}N_3O_2F_4$: C, 55.78; H, 3.18; N, 7.81. Found: C, 55.82; H, 3.41; N, 7.42%.

Example 16

(+)-2-(3,5-Bis(trifluoromethyl)phenyl)-N-[2,3-dihydro-5-(4-fluorophenyl)-2-oxo-1-(2,2,2-trifluoroethyl)-1H-benzo[e][1,4]diazepin-3-yl]-acetamide

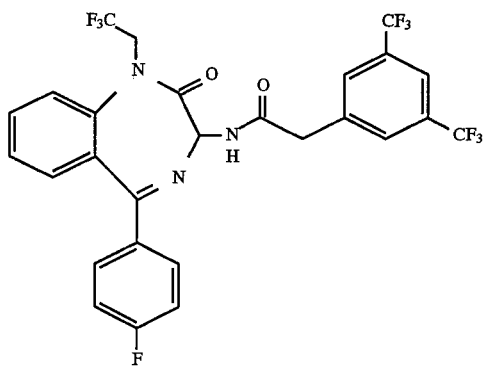

m.p. foam ° C., [α]$_D$=2.8° (c=0.67; MeOH).

Anal. Calcd. for $C_{27}H_{17}N_3O_2F_{10}$: C, 53.56; H, 2.83; N, 6.94. Found: C, 53.56; H, 2.93; N, 6.91%.

Example 17

(–)-2-[2,4-Bis(trifluoromethyl)phenyl]-N-[2,3-dihydro-5-(4-fluorophenyl)-2-oxo1-(2,2,2-trifluoroethyl)-1H-benzo[e][1,4]diazepin-3-yl]acetamide

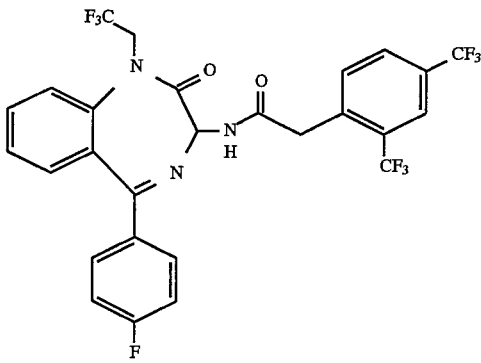

[α]$_D$=–14° (c=0.63; MeOH).

Anal. Calcd. for $C_{27}H_{17}N_3O_2F_{10}$: C, 53.56; H, 2.83; N, 6.94. Found: C, 53.3; H, 2.89; N, 7.05%.

Example 18

3-Cyclohexyl-N-[2,3-dihydro-5-(2-fluorophenyl)-2-oxo-1-(2,2,2-trifluoroethyl-1H-benzo[e][1,4]diazepin3-yl]propionamide

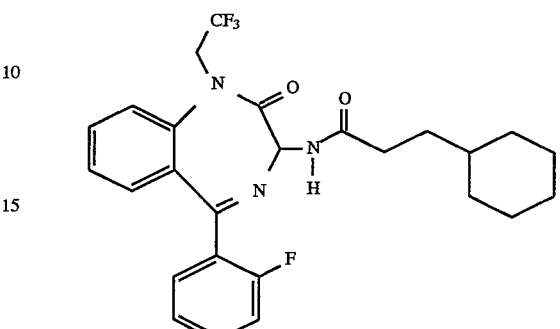

m.p. 202°–204 °C.

$^1$H NMR δ(CDCl3) 7.72 (m,8H), 5.65 (d,J=8.3 Hz, 1H), 5.35–5.08 (m,1H), 4.32–4.15 (m, 1H), 2.37 (t,J=7.8 Hz,2H), 1.80–1.55 (m,7H), 1.45–

Anal. Calcd. for $C_{26}H_{27}F_4N_3O_2$: C, 63.8; H, 5.56; N, 8.58. Found: C, 63.82; H, 5.54; N, 8.56%.

Example 19

3,4-Dichloro-N-[2,3-dihydro-5-(2-fluorophenyl)-2-oxo-1-(2,2,2-trifluoroethyl)-1H-benzo[e][1,4]diazepin-3-yl]benzamide

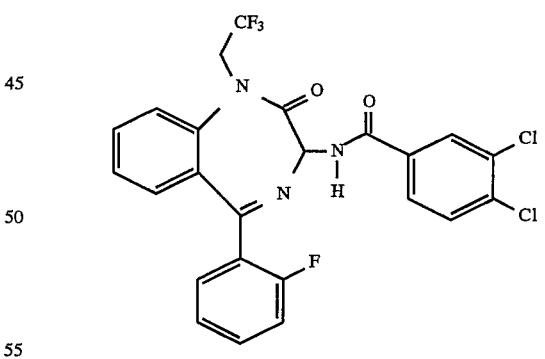

m.p. 168°–170 °C.

$^1$H NMR δ(CDCl3) 8.03 (d,J=2.0,1H), 7.86 (d,J=7.8 Hz, 1H), 7.78–7.05 (m,9H), 5.80 (d,J=7.8 Hz,1H), 5.27–5.15 (m, 1H), 4.35–4.20 (m,1H)

Anal. Calcd. for $C_{24}H_{15}Cl_2F_4N_3O_2$: C, 54.98; H, 2.88; N, 8.01. Found: C, 54.96; H, 2.89; N, 8.12%.

What is claimed is:
1. A compound of the structural formula I

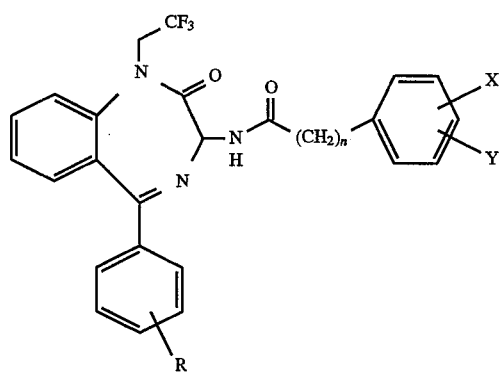

where

X and Y are independently hydrogen, chloro, fluoro, bromo, iodo, or trifluoromethyl and n is 0, 1 or 2;

R is hydrogen, fluoro, chloro, bromo, iodo, or trifluoromethyl, methyl, or methoxy; and the racemates, mixtures of enantiomers, individual enantiomers and pharmaceutically acceptable salts, hydrates or crystal forms thereof.

2. The compound of claim 1 selected from the group consisting of:

(−)-2-[2,4-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide

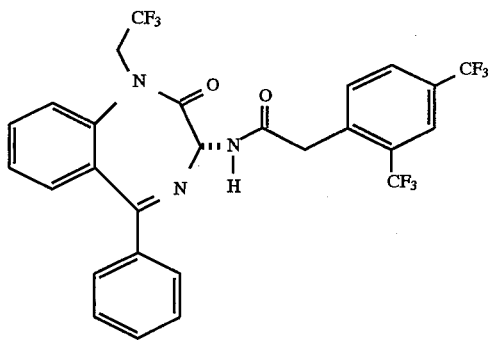

(+)-3,5-Dichloro-N-[3R-2,3-dihydro 2-oxo-5-phenyl-1-(2,2,2-trifluoroethyl)-1H-benzo[e][1,4]diazepin-3-yl]benzamide;

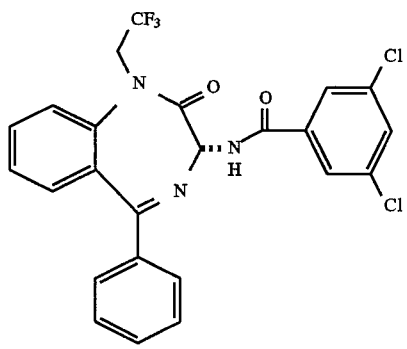

(−)-3,4-Dichlorophenyl-1-yl-N-[3R-2,3-dihydro-2-oxo-5-phenyl-1-(2,2,2-trifluoroethyl)-1H-benzo[e][1,4]diazepin-3-yl]acetamide;

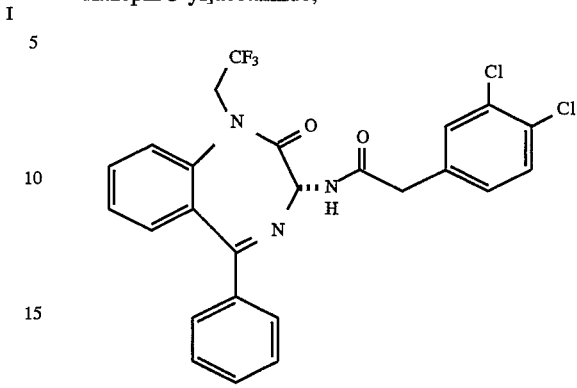

(−)-2-(3,5-Dichlorophenyl)-N-[3R-2,3-dihydro-2-oxo-5-phenyl-1-(2,2,2-trifluoro-ethyl)-1H-benzo[e][1,4]diazepin-3-yl]acetamide

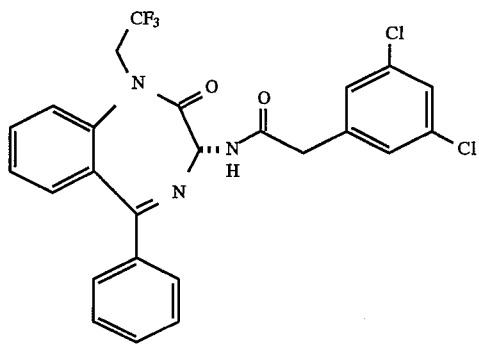

3,4-Dichloro-N-[2,3-dihydro-5-(2-fluorophenyl)-2-oxo-1-(2,2,2-trifluoroethyl)-1H-benzo[e][1,4]diazepin-3-yl]benzamide

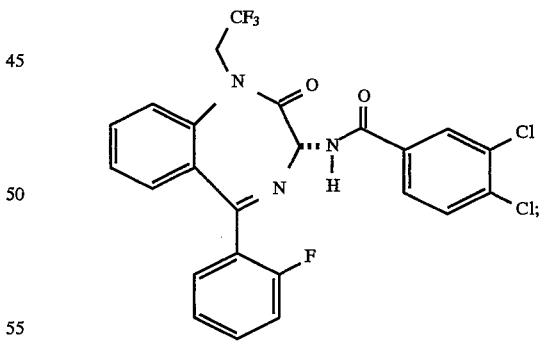

(−)-2-[3,5-Bis(trifluoromethyl)phenyl]-N-[3R-2, 3-dihydro-2-oxo-5-phenyl-1-(2,2,2-trifluoroethyl)-1H-benzo[e][1,4]diazepin-3-yl]acetamide

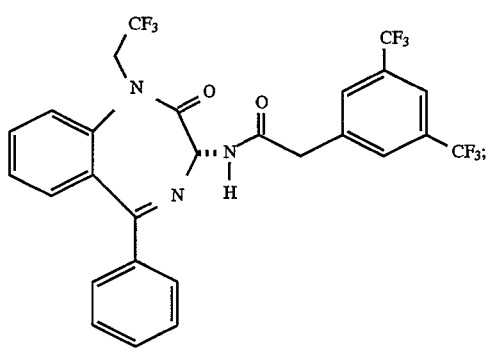

(−)-2-(4-Trifluoromethylphenyl)-N-[3R-2,3-dihydro-2-oxo-
5-phenyl-1-(2,2,2-trifluoroethyl)-1H-benzo[e][1,4]
diazepin-3-yl]acetamide

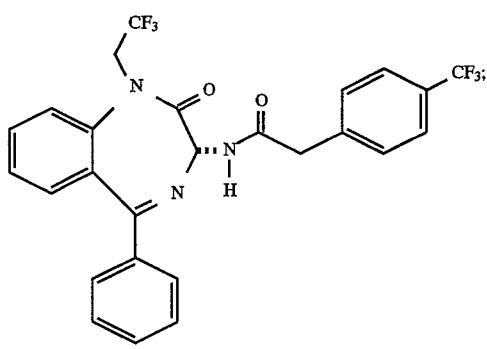

(−)-2-(3-Trifluoromethylphenyl)-N-[3R-2,3-dihydro-2-oxo-
5-phenyl-1-(2,2,2-trifluoroethyl)-1H-benzo[e][1,4]
diazepin-3-yl]acetamide

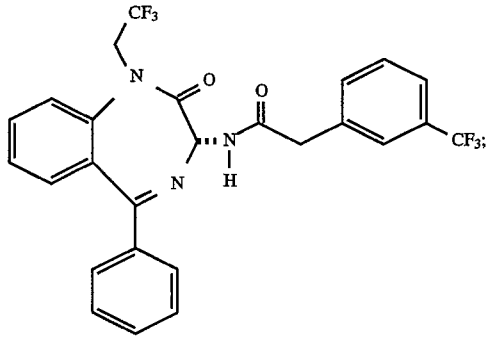

(−)-2-(2-Trifluoromethylphenyl)-N-[3R-2,3-dihydro-2-oxo-
5-phenyl-1-(2,2,2-trifluoroethyl)-1H-benzo[e][1,4]
diazepin-3-yl]acetamide

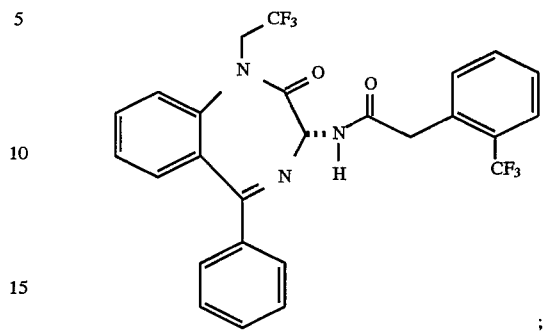

;

(−)-2-(2,4-Dichlorophenyl)-N-[3R-2,3-dihydro-1-(2,2,2-
trifluoroethyl)-2-oxo-5-phenyl-1H-benzo[e][1,4]
diazepin-3-yl]acetamide

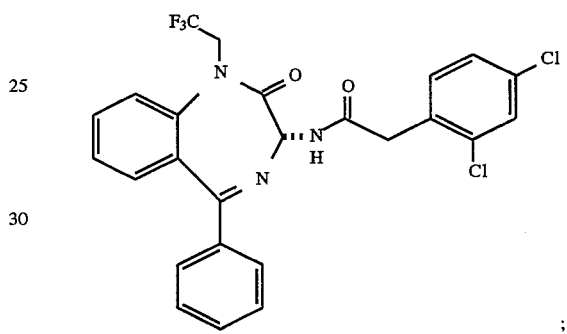

;

(−)-2-(3-Chlorophenyl)-N-[3R-2,3-dihydro-2-oxo-5-
phenyl-1-(2,2,2-trifluoroethyl)-1H-benzo[e][1,4]
diazepin-3-yl]acetamide

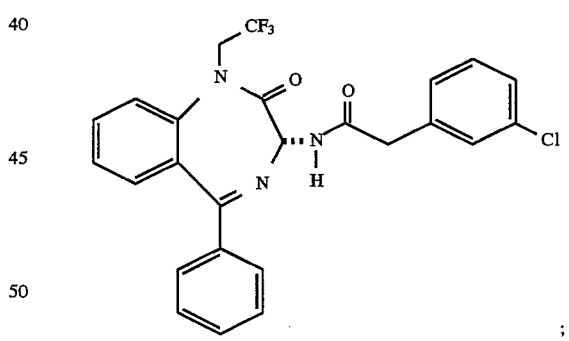

;

29

(−)-2-(4-Chlorophenyl)-N-[3R-2,3-dihydro-2-oxo-5-phenyl-1-(2,2,2-trifluoroethyl)-1H-benzo[e][1,4]diazepin-3-yl]acetamide

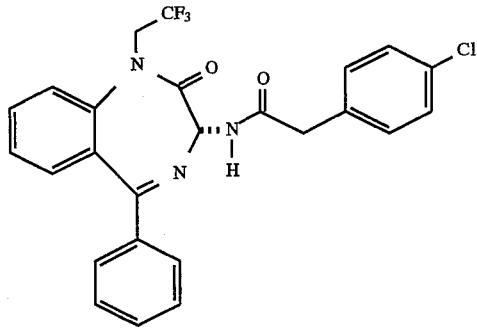

;

(+)-2-(3,5-Dichlorophenyl)-N-[2,3-dihydro-5-(4-fluorophenyl)-2-oxo-1-(2,2,2-trifluoroethyl)-1H-benzo[e][1,4]diazepin-3-yl]-acetamide

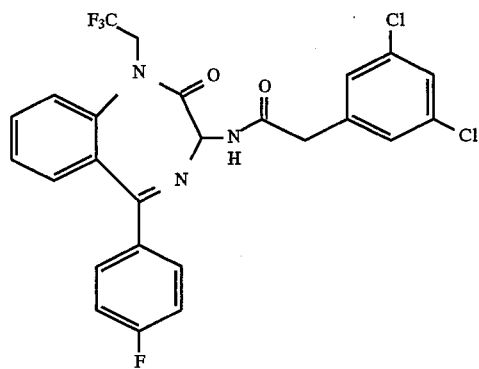

;

(−)-2-(2,4-Dichlorophenyl)-N-[2,3-dihydro-5-(4-fluorophenyl)-2-oxo-1-(2,2,2-trifluoroethyl)-1H-benzo[e][1,4]diazepin-3-yl]acetamide

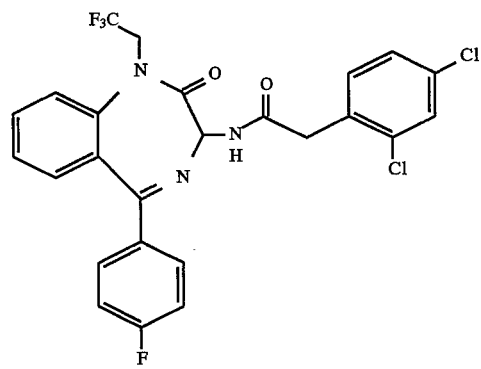

;

30

(+)-2-[3,5-Bis(trifluoromethyl)phenyl]-N-[2,3-dihydro-5-(4-fluorophenyl)-2-oxo-1-(2,2,2-trifluoroethyl)-1H-benzo[e][1,4]diazepin-3-yl]acetamide

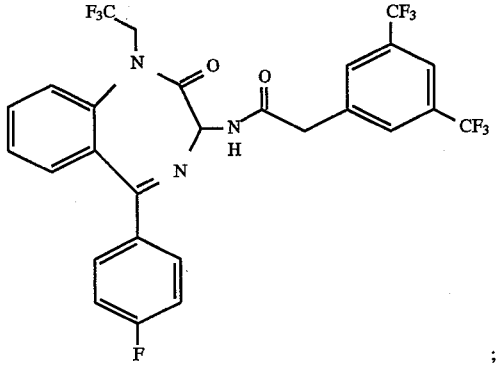

;

(−)-2-[2,4-Bis(trifluoromethyl)phenyl]-N-[2,3-dihydro-5-(4-fluorophenyl)-2-oxo-2,2,2-trifluoroethyl)-1H-benzo[e][1,4]diazepin-3-yl]acetamide

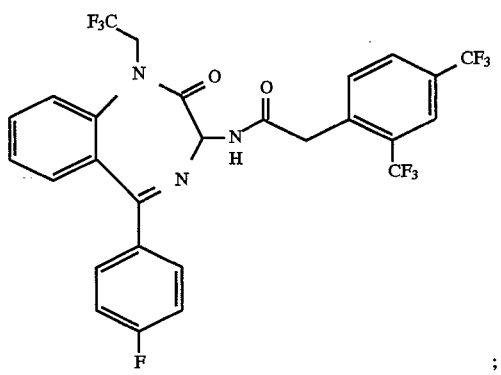

;

(±)-2-(3,5-Dichlorophenyl)-N-[2,3-dihydro-2-oxo-5-phenyl-1-(2,2,2-trifluoroethyl)-1H-benzo[e][1,4]diazepin-3-yl]acetamide

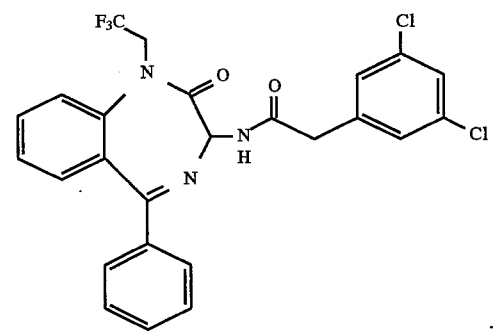

3. The compound of claim 1 which is (+)-3,5-Dichloro-N-[3R-2,3-dihydro-2-oxo-5-phenyl-1-(2,2,2-trifluoroethyl)-1H-benzo[e][1,4]diazepin-3-yl]benzamide

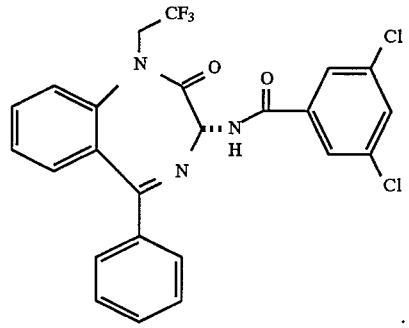

4. The compound of claim 1 which is (−)-2-(3,4-Dichlorophenyl)-N-[3R-2,3-dihydro-2-oxo-5-phenyl-1-(2,2,2-trifluoroethyl)-1H-benzo[e][1,4]diazepin-3-yl] acetamide:

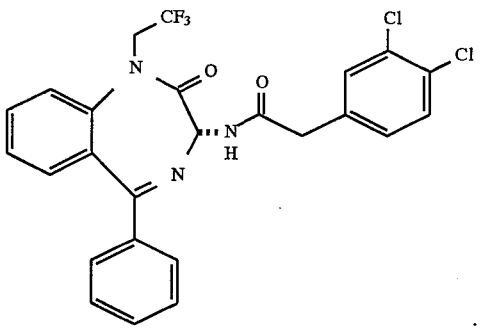

5. The compound of claim 1 which is (−)-2-(3,5-Dichlorophenyl)-N-[3R-2,3-dihydro-2-oxo-5-phenyl-1-(2,2,2-trifluoroethyl)-1H-benzo [e][1,4]diazepin-3-yl] acetamide

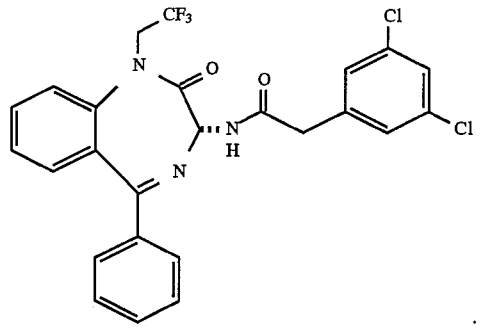

6. The compound of claim 1 which is (−)-2-[2,4-Bis(trifluoromethyl)phenyl]-N-[3R-2,3-dihydro-2-oxo-5-phenyl-1-(2,2,2-trifluoroethyl)-1H-benzo[e][1,4]diazepin-3-yl]acetamide

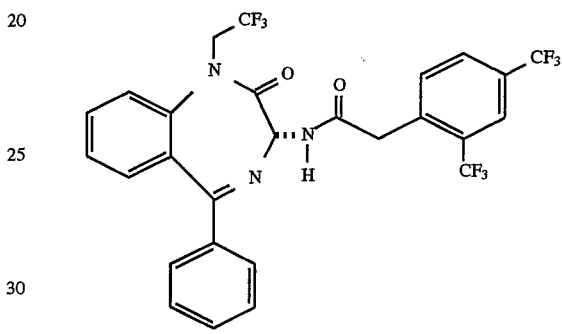

7. A pharmaceutical formulation comprising a pharmaceutically acceptable carrier and a antiarrhythmically effective amount of the compound of claim 1 or a pharmaceutically acceptable salt, crystal form or hydrate thereof.

8. A method of preventing or treating arrhythmia which comprises the administration to a patient in need of such treatment of an antiarrhythmically effective amount of the compound of claim 6.

9. A method of preventing or treating arrhythmia which comprises the administration to a patient in need of such treatment of an antiarrhythmically effective amount of the compound of claim 1.

10. A pharmaceutical formulation comprising a pharmaceutically acceptable carrier and a antiarrhythmically effective amount of the compound of claim 6 or a pharmaceutically acceptable salt, crystal form or hydrate thereof.

* * * * *